(12) United States Patent
Zour et al.

(10) Patent No.: US 10,247,726 B2
(45) Date of Patent: Apr. 2, 2019

(54) HAZARDOUS MATERIAL DETECTION AND ISOLATION DISTANCE APPARATUS AND METHOD

(71) Applicants: John R Zour, Manchester, MD (US); Chad Matthew McClintock, Littlestown, PA (US)

(72) Inventors: John R Zour, Manchester, MD (US); Chad Matthew McClintock, Littlestown, PA (US)

( * ) Notice: Subject to any disclaimer, the term of this patent is extended or adjusted under 35 U.S.C. 154(b) by 0 days.

(21) Appl. No.: 14/252,729

(22) Filed: Apr. 14, 2014

(65) Prior Publication Data

US 2015/0293079 A1 Oct. 15, 2015
US 2016/0363585 A9 Dec. 15, 2016

Related U.S. Application Data

(60) Provisional application No. 61/811,794, filed on Apr. 14, 2013.

(51) Int. Cl.
*G01N 31/22* (2006.01)
*G01N 33/52* (2006.01)

(52) U.S. Cl.
CPC ........... *G01N 33/526* (2013.01); *G01N 31/22* (2013.01)

(58) Field of Classification Search
CPC ............................ G01N 33/526; G01N 31/22
See application file for complete search history.

(56) References Cited

U.S. PATENT DOCUMENTS

| | | | | |
|---|---|---|---|---|
| 3,681,027 A | * | 8/1972 | Smith | G01N 21/78 422/510 |
| 6,284,198 B1 | * | 9/2001 | Kirollos | G01N 21/783 422/401 |
| 7,476,874 B2 | * | 1/2009 | Patel | 250/484.5 |
| 7,504,958 B1 | * | 3/2009 | Genovese | G01N 1/2202 340/632 |
| 2007/0238192 A1 | * | 10/2007 | Locke | B01L 9/52 436/169 |

FOREIGN PATENT DOCUMENTS

WO     WO 2010/019756 A2 *  2/2010

* cited by examiner

*Primary Examiner* — Robert J Eom

(57) ABSTRACT

Disclosed herein is a first responder hazardous material detection and isolation distance (HMDID) apparatus and method that addresses the disconnect that exists in two current first responder tools: a means for detecting a hazardous material, but also the need for an immediate action plan to secure a dangerous area and prevent harm to individuals, such as first responders present at an emergency scene. The detection apparatus comprises test membranes configured to detect a hazardous material present in the atmosphere, by producing a visual color change when exposed to air contaminated with the hazard. The test membranes are attached to a planar form, such as a flat paper card, and are accompanied by an isolation indicator and action item for isolating an area depending on the level of hazardous material present in the atmosphere.

2 Claims, 4 Drawing Sheets

RESIST RUSHING IN!

◆ Rescue attempts must be weighed against you becoming part of the problem

◆ Use this card IN ADDITION to a four gas meter (O2, LEL, H2S & CO)

◆ Distances reflect area SURROUNDING the incident in which persons may be exposed to dangerous (upwind) and life threatening (downwind) concentrations of material that is NOT on FIRE. Adjustments should be made by technically qualified individuals ONLY!

Improvised Explosive Device Preliminary Safe Standoff Distance

| Threat Description | Building Evacuation Distance | Outdoor Evacuation Distance |
|---|---|---|
| Pipe Bomb | 70 ft | 850 ft |
| Suicide Belt | 90 ft | 1080 ft |
| Suicide Vest | 110 ft | 1360 ft |
| Briefcase/Suitcase Bomb | 150 ft | 1850 ft |
| Compact Sedan | 320 ft | 1500 ft |
| Sedan | 400 ft | 1750 ft |
| Passenger / Cargo Van | 640 ft | 2750 ft |
| Small Moving Van | 860 ft | 3750 ft |
| Moving Van | 1240 ft | 6500 ft |
| Semitrailer | 1570 ft | 7000 ft |

High Explosives (TNT Equivalent)

FIG. 4

HAZARDOUS MATERIAL DETECTION AND ISOLATION DISTANCE APPARATUS AND METHOD

CROSS REFERENCE TO RELATED APPLICATION

This patent application claims priority to U.S. Provisional Patent Application No. 61/811,794 filed on Apr. 14, 2013, the contents of which are hereby incorporated by reference in its entirety.

FIELD OF INVENTION

This application relates to the technical field of the detection of hazardous materials, particularly airborne hazardous materials encountered by first responders under emergency situations.

BACKGROUND

First responders find themselves in a changing work environment post-9/11. No longer are the hazards house fires and car crashes; the hazards are scenarios that present quite of variety of extreme dangers, to both persons and property. Incidents involving chemicals such as chemical suicide, clandestine drug labs, train, truck and car crashes involving hazardous materials are all examples of incidents that first responders encounter on a daily basis.

Furthermore, often, hazardous situations are encountered that require immediate identification of hazardous materials that may otherwise go undetected, and an immediate action plan for securing an area to prevent or mitigate potential loss of life or property. For example a standard electronic 4-gas meter ($O_2$, LEI. $H_2S$, CO) would not identify the corrosive environment of an ammonium gas leak at an incident scene. Given the frequency and potentially catastrophic consequences of not identifying the hazards present, there is the need for an easy to use detection methodology, with action items appropriate for the first responder.

SUMMARY OF THE INVENTION

An apparatus/toolkit for detecting exposure to at least one hazardous material or substance is provided, as well as an isolation distance for securing an area in which the hazard is detected. The present invention addresses the disconnect that exists between economic detection methodology for hazardous materials, and the information contained in standard first responder training and educational references, such as the Emergency Responders Guide and NIOSH Pocket Guide to Chemical Hazards, in an easy to use and easy to view format. Often there are means for the detection of chemical or hazardous materials, but what is lacking is a portable detection apparatus that also contains an easy to follow action plan for dealing with potentially life-threatening and dangerous situations, once a positive result for a hazardous material result is realized.

Described herein is a hazardous material detection tool and apparatus comprising a hazardous material (hazmat) detection means. The hazmat detection means comprises at least one detection membrane configured to change color upon the detection of a predetermined hazardous material present in the air (aerosolized) at a threshold level. In one embodiment, the threshold level is a level indicating a hazardous amount, whereby the amount presents a danger to persons or property in the immediate area. Dangers include inhalation dangers or dangers related to fire or explosions.

In another embodiment, the detection apparatus further comprises an associated action item unique to the predetermined hazmat for which the membrane is configured. In one embodiment, the action item provides a first responder with an action for isolating and securing—at a designated distance—an area surrounding that in which the hazardous material is present.

Also described is a method for detecting at least one predetermined hazardous material using a detection tool, comprising presenting at least one membrane configured to detect the presence of a pre-determined hazardous material in the air in an area where there is a need to determine the presence of a hazardous material, monitoring the at least one membrane configured to detect the presence of a hazardous material, detecting, by visual inspection, the presence of a color change of at least one of the membranes, thereby indicating the presence of at least one hazardous material, following the action item associated with the membrane, and isolating the area surrounding the hazardous material.

The present invention is the combination of the means of detection of a hazardous material and the corresponding isolation distance for which to secure an area around the hazard. There is a need for an easy to use detection means that allows a user to read results instantly and have an action plan in place during emergency situations in the field.

BRIEF DESCRIPTION OF THE DRAWINGS

The detailed description is described with reference to the accompanying drawings. In the drawings, the left-most digit of a reference number identifies the figure to which the reference number first appears.

FIG. 4 shows optional hazardous information that can be included on the apparatus as additional hazard information for consideration by a user.

DETAILED DESCRIPTION OF THE INVENTION

Figure 1:
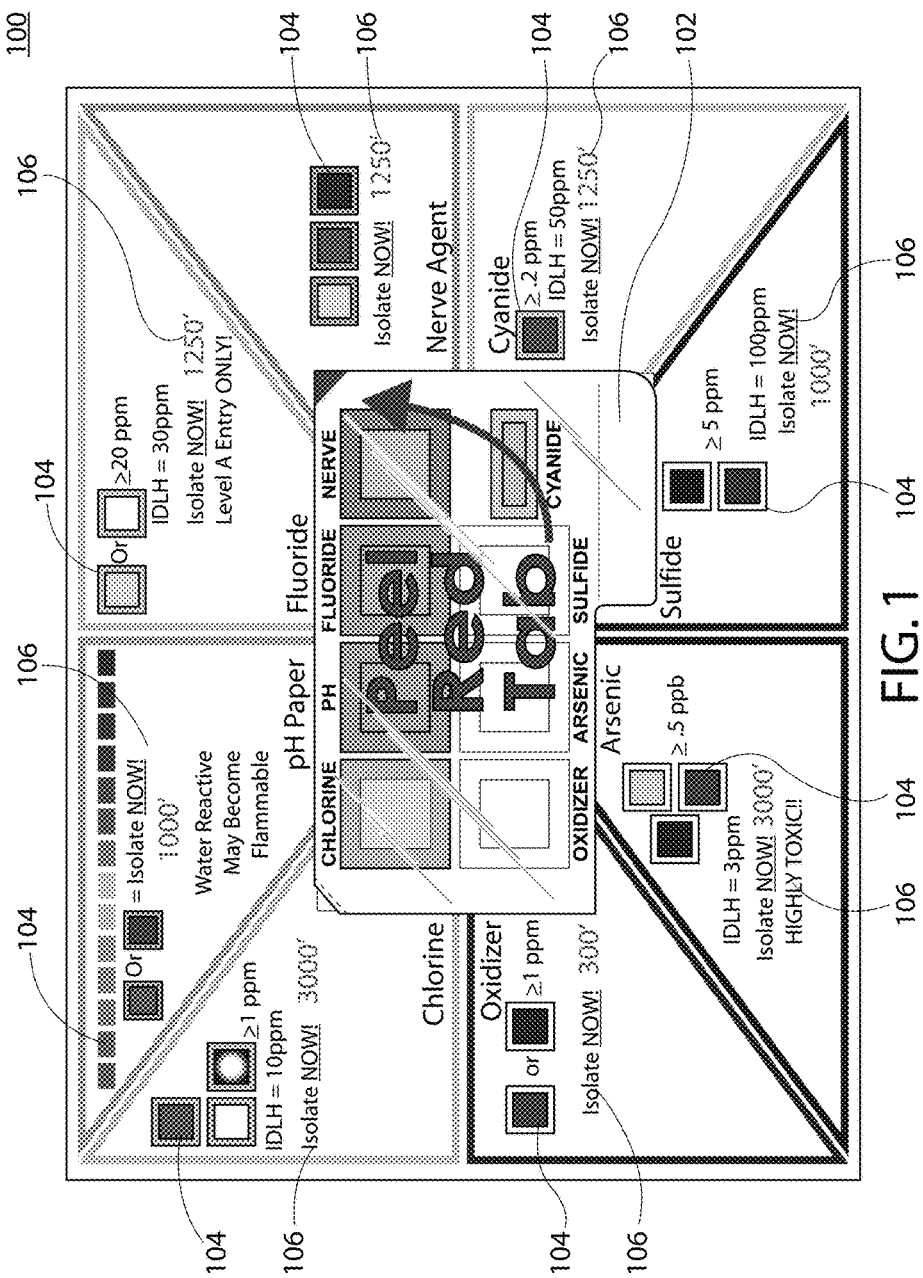
FIG. 1 shows the hazardous material detection and isolation distance (HMDID) apparatus.

First responders find themselves in a changing work environment post-9/11. No longer are the hazards, house fires and car crashes; they are scenarios that present quite of variety of hazards. Incidents involving chemicals such as chemical suicide, clandestine drug labs, train, truck and car crashes involving hazardous materials are all examples of incidents, first responders encounter on a daily basis. Given the frequency and potentially catastrophic consequences of not identifying the hazards present, the present invention helps to combine easy to use detection methodology with action items appropriate for the first responder. Reagent paper has been in use to detect chemical hazards for some time. There is a significant disconnect, however, between identifying a meaningful color change and more importantly what action should the first responder take. The present invention helps to close this gap.

The first responder hazardous material detection and isolation distance (HMDID) apparatus and method described herein addresses the disconnect that exists in two current first responder tools: a means for detecting a hazardous material, but also the need for an immediate action plan to secure a dangerous area and prevent harm to individuals, such as first responders present at an emergency scene. There are existing guides for action, such as "Emergency Response Guidebook" and "The NIOSH Guide to Chemical Hazards", however, in an emergency where time is of the essence it is not feasible to consult guidebooks. The present invention solves this problem because it presents the ability to detect a hazardous material and simultaneously provide an action plan for dealing with the hazardous material. This is a significant advantage because in a life and death situation there is no time to consult guidebooks to ascertain the best means of dealing with a potential hazard.

In one embodiment, the hazardous material detection and isolation distance HMDID apparatus provides the first responder with a tool capable of detecting many of the hazards that could otherwise go undetected in the line of duty. The HMDID tool detects hazardous materials present in the air (aerosolized) by way of a colorimetric test, and if results are positive, the user can then follow the prompt for isolation distance, based on the hazardous material detected.

In one embodiment, the HMDID apparatus is in the form of a flat card, made from card stock or other fairly rigid material, and is configured with a detection means, in which one or more hazardous materials are detected.

In one embodiment, the detection means include a specially-treated chemically-sensitive membrane that contains the necessary reagents to react with a particular hazardous material present as vapor or in aerosolized form in the atmosphere. In another embodiment, the membranes are hazardous material-specific. If a hazard is present in the air, it will react with the detection reagents embedded in the membrane. A color change of the membrane will indicate the presence of the hazard; no change in color indicates the absence of the hazard, or is an indication that the hazard is not present at a dangerous level that presents a threat to first responders or requires an action plan, such as isolation of the hazard.

In one embodiment, the chemically-sensitive detection membranes are self-contained and individualized for a particular hazard. The membranes can be comprised of paper, and any combination of hydrophilic or hydrophobic material that provide a stable environment for the reagents necessary to detect the airborne hazard. In one embodiment, the membranes are configured as part of the card that makes up the apparatus; in another embodiment, the membranes are reversibly affixed to the apparatus so that they are removable. This allows for replenishment of the apparatus with fresh membranes.

Because the membranes are self-contained they contain all the necessary reagents, buffers, indicators, catalysts necessary to react with airborne hazards. In one embodiment, the membranes are single-use. In another embodiment, as indicated, the membranes are removable and disposable from the apparatus and can be replaced with fresh membranes after each use.

Each chemically-sensitive membrane is configured with a sensitivity threshold—the level at which a hazard in the atmosphere will produce a positive indication by visual means, such as by a change in color or the appearance of a color. This presence or change in color—the visual indication of a hazard—triggers an action item, which is isolation of the area around the hazard. Upon detection of the hazard, the user simply looks to the action instruction presented on the apparatus, which provides the isolation distance for the corresponding hazard. This eliminates the need to consult a reference guide under extremely dangerous circumstances where time is of the essence and decisions must be made in an instant.

In one embodiment, the membranes are in the form of test strips for on-site rapid detection of hazardous materials. In another embodiment, the test strips could be commercially available Haz-Mat Test Strips, distributed by Universal Products, Inc of Salt Lake City, Utah. Other suitable hazard testing material may be used.

In one embodiment, the apparatus is configured to accept the detection membranes on the surface of the card. In another embodiment, each membrane corresponds to a particular chemical hazard and is delineated from other membranes. It is envisioned that multiple membranes can be employed, with each membrane being clearly identified for the hazard it is configured to detect, with the corresponding action item information displayed in adjoining proximity.

The following table provides an overview of one embodiment of the apparatus, specifically the effect of certain types of chemicals with the detection membranes and the corresponding action item.

TABLE 1

| Hazmat Detection | Sensitivity Level | Positive Indication | Isolation |
| --- | --- | --- | --- |
| Chlorine | 1 ppm | White to blue | 3000 feet |
| pH | Above or below neutral | Red or black | 1000 feet |
| Fluoride | 20 ppm | Yellow or white | 1250 feet |
| Nerve | In contact with G, Mustard gas (H), V agents | Mustard, red or black | 1250 feet |
| Oxidizers | 1 ppm | Blue or purple | 300 feet |
| Arsenic | 0.5 ppb | Black, brown or yellow | 3000 feet |
| Hydrogen Sulfide | 5 ppm | Black or brown | 1000 feet |
| Cyanide | 0.2 ppm | blue | 1250 feet |

Turning now to the Figures, FIG. 1 shows one embodiment of a hazardous material detection and isolation distance (HMDID) apparatus. Apparatus 100 is configured with detection means 102, isolation indicators 104, and action items 106. Optionally included along with the isolation indicators 104 and action items 106 are a corresponding cross-reference and citation index 108 to reference guides commonly used in the field, such as the Emergency Response Guidebook, should additional information be desired. This additional cross-reference and citation index 108 can be included on the apparatus; for example, Table 3 on page 124 of the ERG contains additional information for Chlorine (based on the 2012 edition). Citations will vary, however, based on the reference manual used and the edition of the manual.

Detection means 102 comprise at least one membrane configured for the detection of a pre-determined hazardous material. Hazardous materials include one or more of the following: chlorine, pH, fluoride, nerve agents, cyanide, sulfide, arsenic, and/or oxidizers. Detection means 102 produce a visible color change if the pre-determined hazardous material is present in the air (aerosolized form) at a threshold level (see Table 1). In one embodiment, detection means 102 are a membrane pre-treated with reagents and/or buffers and/or catalysts needed to react with a particular chemical hazard. The membranes are covered with a protective barrier, such as a plastic film or other protective means, in order to preserve the membrane and provide stability to the reagents. The membranes are activated upon the removal of the protective barrier and exposed to the environment.

Isolation indicators 104 provide the first responder with means to compare the result of the detection means against a standard level at which action item 106 should be initiated. For example, the isolation indicators display the level at which a hazardous material present in the environment is at a level requiring isolation. The isolation indicator represents the danger level for a hazardous material, thus if the first responder sees a visual color change to the detection membrane that corresponds to a high threat level shown by the isolation indicator, it is a trigger to the first responder to follow the action item 106 associated with the corresponding detection means 102.

In one embodiment, the following isolation indicators are used to trigger the action item for the corresponding hazardous material: pH detection isolation indicator is the color red or black, which triggers a corresponding action item of isolation displayed within the pH panel; Fluoride detection isolation indicator is the color yellow or white, which triggers a corresponding action item of isolation listed within the Fluoride panel; Nerve agent detection isolation indicator is one of the colors mustard, red or dark blue; Cyanide detection isolation indicator is the color blue; Arsenic detection isolation indicator is one of the color yellow, brown or black; Oxidizers detection isolation indicator is one of the color blue or purple; Chlorine detection isolation indicator is one of the colors in a range of white to blue.

For example, if the detection means 102 for pH, upon exposure to the environment produces a visual color change that matches the isolation indicator 104—in this example red or black—then action item 106 is initiated and the first responder will isolate the area according to the action item 106—in this example 1000 feet.

Detection means 102 are shown in FIG. 1 as arranged in the center of the apparatus 100, with isolation indicators 104 and action items 106 arranged outwardly around the perimeter of the detection means 102. Other arrangements are possible and envisioned. In one embodiment, apparatus 100 is in paper form, but could be comprised of other natural or synthetic materials. The apparatus 100 can also be configured with attachment means, such as Velcro or straps which allow a first responder to attach the apparatus 100 to other pieces of equipment, such as equipment worn and used during an emergency situation where the detection of atmospheric hazardous materials is necessary.

In one embodiment, apparatus 100 is in the form of an essentially-flat paper form, such as a card, and can be of varying size and shape. FIG. 1 shows one embodiment of the form, with a rectangular shape. In another embodiment, the size of the rectangular form is approximately the size of a 5×7 rectangular sheet of paper. The size is variable, however, provided the size is commensurate with the number of membranes affixed and the corresponding action items needed for the number of membranes contained thereon.

Figure 2:
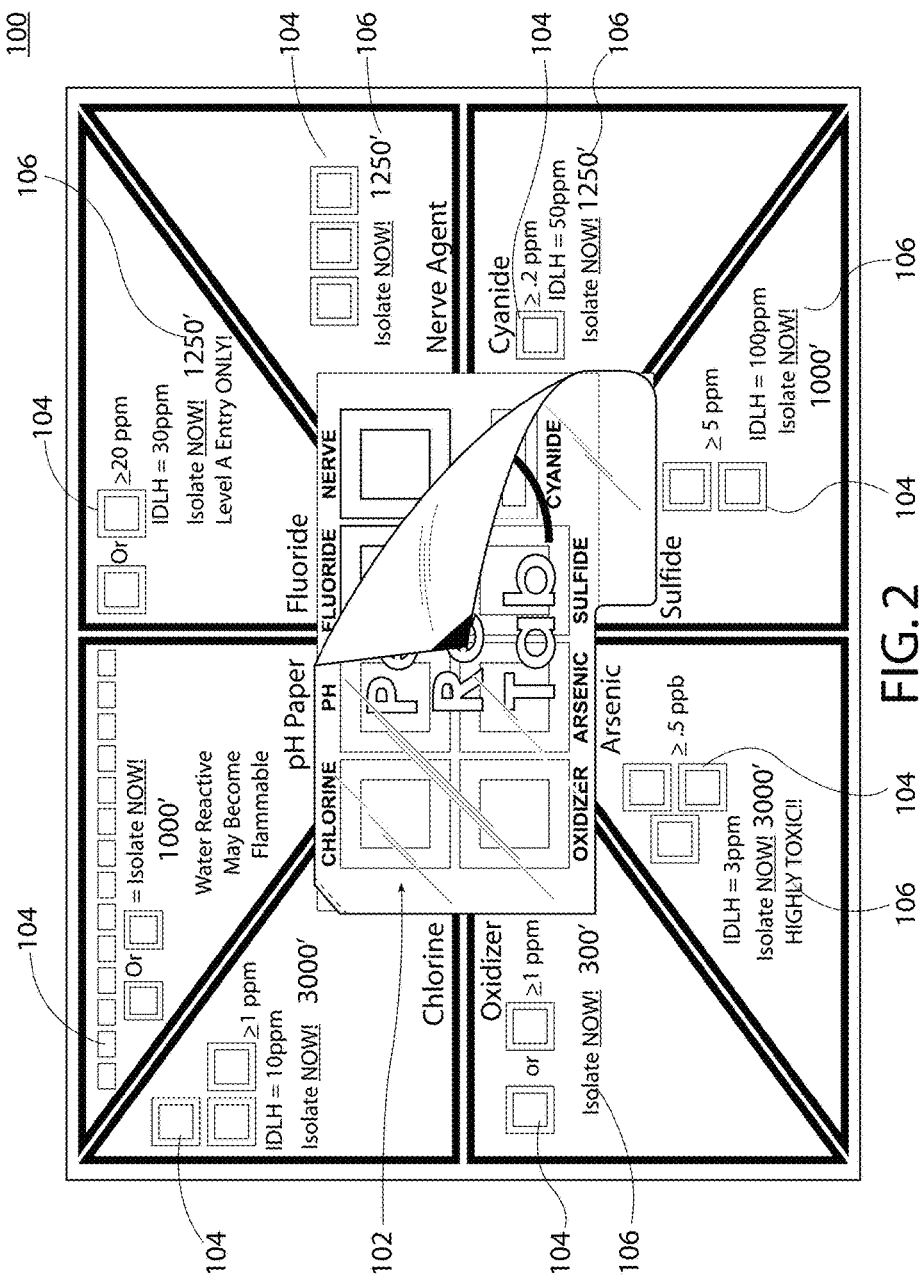
FIG. 2 shows the hazardous material detection and isolation distance (HMDID) apparatus with the protective film covering partially pulled back away from the detection membranes.

FIG. 2 shows the protective layer having been partially peeled, therefore exposing the test membranes to the environment in which hazardous materials may be present.

Figure 3:
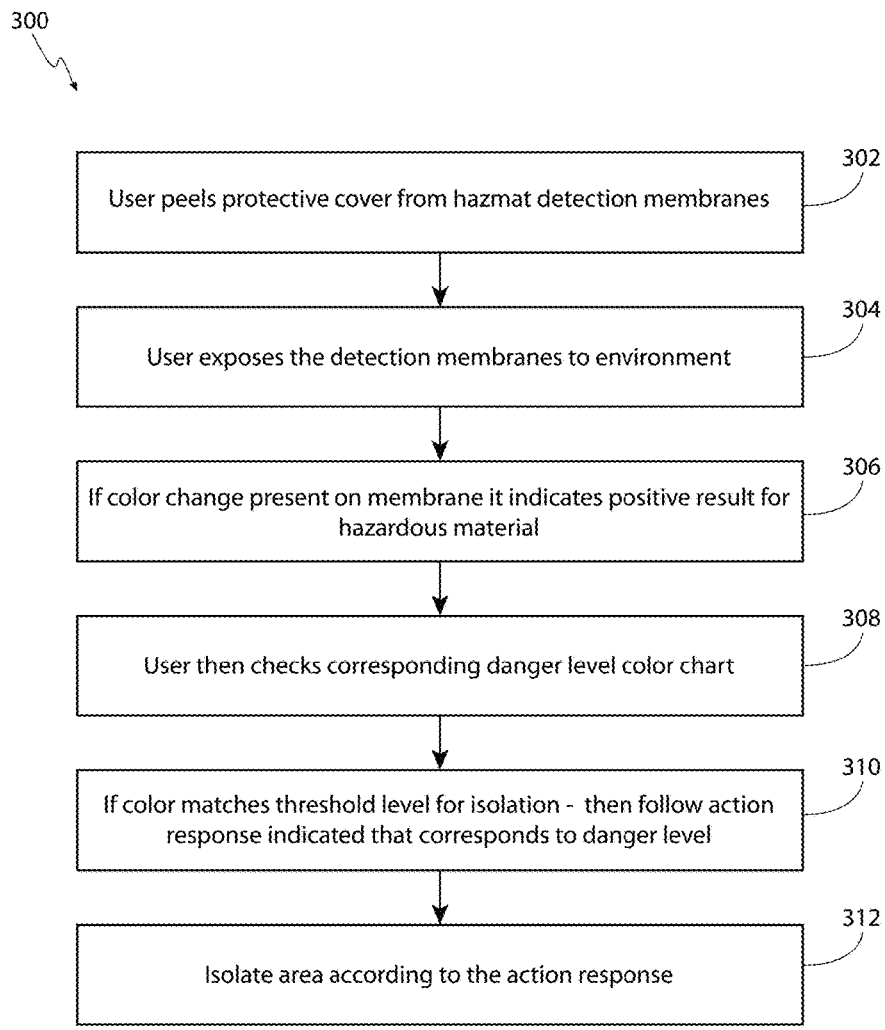
FIG. 3 shows a flowchart of the method for detecting the presence of a hazardous material and corresponding action item depending on the hazardous material detected.

FIG. 3 shows a flowchart of the steps involved in a method of detecting a hazardous material using one embodiment of the present invention in the form of a Haz-mat Detection card (referred to also as the Z-Mac Device).

One particular embodiment of the invention can be carried out by a user by following a method comprising the following steps:
1. Expose the membrane/reagent paper to the atmosphere that the first responder seeks to sample;
2. Determine a "meaningful" color change by observing the membrane/reagent paper and cross referencing the color seen on the membrane with the isolation indicator index (boxed colors) on the card (apparatus);
3. If a match exists between the membrane/reagent paper and the isolation indicator (boxed color), that chemical is present in the air at the minimum level provided;
4. Follow the action item isolation distances listed on the card until qualified personnel can further adjust isolation distances;
5. May be used with the Emergency Response Guidebook (ERG) as guide numbers and appropriate tables are provided on the card;
6. The reverse side of the Z-Mac card provides a table for first responders to utilize in dealing with the need to determine isolation distances when there is an Improvised Explosive Device (IED) suspected; and, optionally,
7. In some chemical categories, the Z-Mac card provides the user with additional hazard information that should be taken into consideration by the first responder (i.e. may become flammable, may be water reactive, level A entry only).

Reference herein to "example", "embodiments" or similar formulations means that a particular feature, structure, operation or characteristic described in connection with the example, is included in at least one implementation in this description. Thus, the appearance of such phrases herein is not necessarily all referring to the same example. Further, various particular features, structures, operations or characteristics may be combined in any suitable manner in one or more examples, and or embodiments.

Although features of the invention have been described in the context of the various embodiments set forth herein, those skilled in the art will appreciate that changes and modifications may be made to the described embodiments without departing from the spirit and scope of the invention.

We claim:
1. A method for a first responder to immediately detect a plurality of aerosolized chemical hazards and determine the minimum safe isolation distance associated therewith, the method consisting essentially of:
  providing an apparatus for the immediate detection and identification of a plurality of aerosolized chemical hazards, the apparatus consisting essentially of:
    a substantially flat card having a front surface and a rear surface;
    a plurality of chemically sensitive detection membranes integrated into the front surface and configured to detect on contact at least one of the plurality of aerosolized chemical hazards in the local atmosphere when present at a threshold level, wherein each of the chemically sensitive detection membranes changes color upon contact with the threshold level of the aerosolized chemical hazard it is configured to detect;
    a plurality of optical apertures integrated into the rear surface, the plurality of optical apertures having such sizes, shapes and locations to enable the first responder to see the plurality of chemically sensitive detection membranes;

a color change intensity scale for each of the plurality of chemically sensitive detection membranes, visible at the rear surface; and at least one recommended action visible at the rear surface and corresponding to the color change intensity of each of the plurality of chemically sensitive detection membranes, wherein the at least one recommended action comprises a) establishing a safe isolation distance from a detected aerosolized chemical hazard b) preventing human exposure to the detected aerosolized chemical hazard or c) a combination thereof;

exposing the apparatus to a local atmosphere; and establishing a safe isolation distance from the detected aerosolized chemical hazard, preventing human exposure to the detected aerosolized chemical hazard, or a combination thereof.

2. The method of claim 1, wherein the apparatus further comprises a list of secondary hazards corresponding to one or more color intensities present on the color change intensity scale.

\* \* \* \* \*